United States Patent [19]

Lapporte et al.

[11] Patent Number: 5,008,451
[45] Date of Patent: Apr. 16, 1991

[54] METHYLENE AND OXYMETHYLENE BIS-ESTER PRODUCTION

[75] Inventors: Seymour J. Lapporte, Orinda; William G. Toland, San Rafael, both of Calif.

[73] Assignee: Chevron Research Company, San Francisco, Calif.

[21] Appl. No.: 428,816

[22] Filed: Oct. 27, 1989

Related U.S. Application Data

[60] Continuation of Ser. No. 400,817, Jul. 22, 1982, abandoned, which is a continuation of Ser. No. 890,560, Mar. 20, 1978, abandoned, which is a continuation of Ser. No. 575,309, May 7, 1975, abandoned, which is a division of Ser. No. 398,732, Sep. 19, 1973, Pat. No. 3,927,078, which is a continuation-in-part of Ser. No. 282,623, Aug. 21, 1972, abandoned.

[51] Int. Cl.$^5$ .............................................. C07C 51/56
[52] U.S. Cl. .................................................... 562/891
[58] Field of Search ......................................... 562/891

[56] References Cited

U.S. PATENT DOCUMENTS

| | | | |
|---|---|---|---|
| 2,727,902 | 12/1955 | Reppe | 260/549 |
| 2,729,651 | 1/1956 | Reppe | 260/549 |
| 2,730,546 | 1/1956 | Reppe | 260/549 |
| 2,789,137 | 4/1957 | Reppe | 260/549 |
| 3,579,551 | 5/1971 | Craddock | 260/549 |
| 3,579,552 | 5/1971 | Craddock | 260/549 |
| 3,717,670 | 2/1973 | Schultz | 260/549 |
| 3,769,324 | 10/1973 | Paulik | 260/549 |
| 3,772,830 | 10/1973 | Paulik | 260/549 |
| 3,821,265 | 6/1974 | Forster | 260/549 |

OTHER PUBLICATIONS

Falbe, CO in Organic Synthesis, 1970, pp. 113–117.

*Primary Examiner*—Robert Gerstl
*Attorney, Agent, or Firm*—Claude J. Caroli; Richard J. Sheridan; T. G. DeJonghe

[57] ABSTRACT

Methylene and oxymethylene bis-esters are produced by the reaction of an aliphatic ester of a carboxylic acid, formaldehyde and carbon monoxide in the presence of a catalytic amount of a Group VIII noble transition metal compound, an iodide or bromide promoter, and a proton donor.

19 Claims, No Drawings

METHYLENE AND OXYMETHYLENE BIS-ESTER PRODUCTION

RELATED APPLICATION

This application is a continuation of application Ser. No. 400,817, filed July 22, 1982, now abandoned, which is a continuation of application Ser. No. 890,560, filed Mar. 20, 1978, now abandoned, which is a continuation of application Ser. No. 575,309, filed May 7, 1975, now abandoned, which is a division of application Ser. No. 398,732, filed Sept. 19, 1973, now U.S. Pat. No. 3,927,078, which is a continuation-in-part of application Ser. No. 282,623, filed Aug. 21, 1972, now abandoned, the disclosures of which are incorporated herein by reference.

BACKGROUND OF THE INVENTION

This invention is related to the preparation of methylene and oxymethylene bis-esters by carbonylation reactions in the presence of transition metal catalysts.

Applicants' U.S. Pat. No. 3,720,706, issued Mar. 13, 1973, and U.S. Ser. No. 302,373, filed Oct. 30, 1972, disclose the preparation of methylene and oxymethylene bis-esters by the reaction of a carboxylic acid, ethylene, carbon monoxide and formaldehyde in the presence of a rhodium catalyst and an iodide or bromide promoter. U.S. Pat. No. 3,702,706 and U.S. Ser. No. 302,373 also disclose the preparation of methylene and oxymethylene bis-propionates directly from ethylene, carbon monoxide, water and formaldehyde in the presence of a rhodium catalyst and an iodide or a bromide promoter.

Tomiska and Spousta, Angew Chem., Int. Ed., 1, 211 (1962) disclose the preparation of methylene and oxymethylene bis-acetates from acetic anhydride and trioxane in the presence of perchloric acid.

Methylene and oxymethylene bis-esters are useful for preserving moist grain during storage, as disclosed by French Pat. No. 70/37,979 of Kensler et al, granted July 12, 1971.

SUMMARY OF THE INVENTION

It has now been found that methylene and oxymethylene bis-esters are produced by the reaction of aliphatic esters of carboxylic acids, formaldehyde and carbon monoxide in the presence of a Group VIII noble transition metal compound, an iodide or bromide promoter, and a proton donor. The net reaction for the process of the invention can be depicted by the following equation (1):

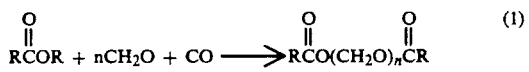

$$RCOR + nCH_2O + CO \longrightarrow RCO(CH_2O)_nCR \quad (1)$$

wherein R is an organic radical and n is a whole integer of from 1 to 5 inclusive.

DESCRIPTION OF THE PREFERRED EMBODIMENTS

The Catalyst System

The catalyst system employed in the process of the present invention comprises a Group VIII noble transition metal compound, an iodide or bromide promoter and a proton donor.

Suitable Group VIII noble transition metal compounds include rhodium, ruthenium, palladium, iridium and platinum compounds. Examples of suitable rhodium compounds include rhodium halides, such as $RhCl_3$, $RhBr_3$ and $RhI_3$; rhodium carbonyl halides, such as $Rh_2(CO)_4Br_2$, $Rh_2(CO)_4Cl_2$ and $Rh_2(CO)_4I_2$; and $Rh_2O_3$. Other suitable rhodium compounds are rhodium coordination compounds containing monodentate ligands, such as carbon monoxide, halides, amines, organophosphines, organoarsines and/or organostibines, i.e., rhodium compounds such as $Rh[(C_6H_5)_3P]_2(CO)I$ and $RhCl(CO)]C_6H_5)_3As]_2$. Examples of ruthenium compounds include ruthenium trichloride and ruthenium dicarbonyl diiodide. Examples of palladium and platinum compounds include palladium oxide, palladium halides such as $PdCl_2$ and $PdBr_2$, palladium carbonyl halides such as $Pd(CO)_2Cl_2$, platinum oxide, palladium acetate, $Pd[(n-C_4H_9)_3P](CO)Cl_2$, and palladium nitrate. Examples of iridium compounds include iridium trichloride, $Ir_2(CO)_4I_2$, and iridium nitrate.

The transition metal catalyst component may be generated in the reaction mixture by providing to the reaction mixture the free transition metal, e.g., Rh, Ru, or Pd metal.

The preferred Group VIII noble transition metal compounds are rhodium and palladium compounds. The particularly preferred transition metal compounds are rhodium compounds, especially rhodium halide and rhodium carbonyl halide compounds.

Suitable iodide promoters include iodine, hydrogen iodide (hydroiodic acid) and alkyl iodides of 1 to 6 carbon atoms and 1 to 3 iodide groups such as methyl iodide, ethyl iodide, methylene di-iodide, iodoform, and isopropyl iodide.

Suitable bromide promoters include bromine, hydrogen bromide, and alkyl bromides of 1 to 6 carbon atoms and 1 to 3 bromide groups such as methyl bromide, methylene dibromide, isopropyl bromide and bromoform.

Certain transition metal compounds such as $RhI[C_6H_5)_3P]_3$, $RhBr_3$, $RhI_3$, $RuI_3$, $Ru(CO)_2I_2$, $PdBr_2$ and $IrI_3$ incorporate iodide and/or bromide moieties, so that a separate iodide or bromide promoter may not be required.

The catalyst system of a Group VIII transition metal compound and an iodide or bromide promoter is a known catalyst combination and is disclosed, for example, in U.S. Pat. Nos. 3,579,551 and 3,579,552, issued to Craddock et al on May 18, 1971, and Canadian Pat. No. 837,640, issued to Paulik et al on Mar. 24, 1970. The disclosures of these patents are hereby incorporated by reference.

In addition to the Group VIII transition metal compound and the iodide or bromide promoter, an essential component of the catalyst system of the process of the invention is a proton donor. The preferred proton donors are water and Bronsted acids such as inorganic acids, e.g., hydroiodic acid, hydrochloric acid, sulfuric acid, phosphoric acid, etc., and organic carboxylic acids, e.g., alkanoic acids of 1 to 6 carbon atoms such as formic acid, acetic acid, propionic acid, butyric acid, valeric acid, hexanoic acid, etc.

When employing an alkanoic acid as the proton donor, the alkanoic acid employed preferably corresponds to the alkanoyl moiety of the methylene or oxymethylene bis-ester product. In one modification of the process, the alkanoic acid is generated in the reaction mixture by the carbonylation of an alkanol of 1 to 5 carbon atoms in the presence of the Group VIII transition metal compound and the iodide or bromide promoter employed in the process of the invention, as disclosed in Canadian Pat. No. 837,643, issued to Paulik et al on Mar. 24, 1970.

Water of crystallization present in transition metal compounds employed in the process suitably serves as the proton donor. Accordingly, when transition metal compounds having water of crystallization are employed, no additional, or less, proton donor is required. Similarly, when the iodide promoter is hydroiodic acid or hydrobromic acid, an additional proton donor is not required.

Molar ratios of the iodide or bromide promoter to the transition metal component of the catalyst system in the range 1:1 to 2500:1 are generally suitable. However, the preferred molar ratios of iodide or bromide promoter to transition metal component are about 3:1 to 300:1, and the most preferred molar ratios are about 5:1 to 100:1.

Molar ratios of proton donor to the transition metal component of the catalyst system in the range of 1:1 to 2500:1 are generally suitable. However, the preferred molar ratios of proton donor to transition metal component are about 3:1 to 300:1 and the most preferred molar ratios are about 5:1 to 100:1.

Concentrations of the transition metal compound of the catalyst system in the reaction medium between $10^{-6}$ mols/liter and $10^{-1}$ mols/liter are normally employed, with the preferred range being $10^{-4}$ mols/liter to $10^{-2}$ mols/liter. Higher concentrations, even to the extent of 1 mol/liter, may, however, be used if desired.

The concentration of the iodide or bromide promoter portion of the catalyst system in the reaction medium may vary widely over the broad concentration range of $10^{-6}$ mols/liter to 18 mols/liter, based on iodide or bromide atom. In the process of this invention, however the preferred concentration range of promoter is $10^{-4}$ mols/liter to 2 mols/liter.

The concentration of the proton donor is generally in the same ranges as defined for the iodide or bromide promoter.

Although the catalyst system is generally employed as a homogeneous catalyst system, components of the catalyst system, e.g., the transition metal compound, may be dispersed on inert supports, such as silica or alumina, to provide a heterogeneous catalyst system.

In certain modifications of the process, minor amounts of a Lewis acid co-catalyst may be employed. However, the Lewis acid co-catalyst is not required, and in the preferred modification of the process, no Lewis acid co-catalyst is employed. When employed, suitable Lewis acid co-catalysts include aluminum trichloride, boron trifluoride, etc.

The Carbon Monoxide Reactant

The carbon monoxide is employed in the process at partial pressures of from about 1 psia to about 5000 psia, although partial pressures of about 25 psia to 2000 psia are preferred. Carbon monoxide streams containing inert impurities such as carbon dioxide, hydrogen, methane, nitrogen and paraffinic hydrocarbons having 1 to 4 carbon atoms may be employed, if desired.

The Carboxylic Acid Ester Reactant

The process of the invention is broadly applicable to aliphatic esters of any carboxylic acid. Suitable carboxylic acid esters include aliphatic esters of carbocyclic aromatic acids such as benzoic acid, phenylacetic acid, terephthalic acid (mono- or di-ester) and naphthoic acid; substituted-carbocyclic aromatic acids such as p-chlorobenzoic acid, 3-(p-bromophenyl)-propionic acid, etc., and substituted-aliphatic acids such as trichloroacetic acid, perfluoroacetic acid, etc.

One class of preferred carboxylic acid ester reactants are aliphatic esters of hydrocarbon carboxylic acids represented by the formula (I):

wherein $R^1$ is vinyl or an alkyl group of 1 to 10 carbon atoms, preferably 1 to 6 carbon atoms, and $R^2$ is hydrogen, an alkyl group of from 1 to 10 carbon atoms, preferably from 1 to 6 carbon atoms, or a hydrocarbyl monocyclic aryl group of from 6 to 10 carbon atoms.

Representative alkyl groups which $R^1$ and $R^2$ may represent include methyl, ethyl, propyl, isopropyl, butyl, pentyl, hexyl, octyl, decyl, etc. Representative aryl $R^2$ groups include phenyl, alkylphenyl groups of 7 to 10 carbon atoms such as tolyl, xylyl, 2,4-diethylphenyl, t-butylphenyl, etc; phenylalkyl groups of 7 to 10 carbon atoms such as benzyl, 3-phenylpropyl, 2-phenylbutyl, etc.

The preferred $R^1$ and $R^2$ groups are linear alkyl groups of 1 to 4 carbon atoms. The particularly preferred $R^1$ and $R^2$ group is methyl.

Illustrative carboxylic acid esters of formula (I) include methyl formate, ethyl formate, vinyl acetate, methyl acetate, methyl propionate, methyl decanoate, ethyl propionate, propyl butyrate, isopropyl isobutyrate, butyl pentanoate, ethyl octanoate, methyl benzoat methyl 3,5-dimethylbenzoate, methyl 4-methylbenzoate, ethyl benzoate, propyl 2,4-dimethylbenzoate, methyl 2-phenylacetate, methyl 3-phenylpropionate and ethyl 3-tolylpropionate.

The preferred carboxylic acid esters of formula (I) are methyl esters ($R^1$=methyl) and particularly preferred esters are methyl alkanoates ($R^1$=methyl, $R^2$=alkyl).

The carboxylic acid ester reactant is suitably provided to the reaction mixture as the preformed material or is generated in situ in the reaction mixture. In one modification of the process, the ester reactant is generated in situ directly in the reaction mixture from ethers of the formula $R^1OR^2$ wherein $R^1$ and $R^2$ are alkyl and/or aryl groups as defined in formula I. In a preferred modification of the reaction, alkyl alkanoate reactants (i.e., $R^1$ and $R^2$ are alkyl) are generated in situ from dialkyl ethers, especially dialkyl ethers wherein both alkyl are the same linear alkyl group of 1 to 4 carbon atoms.

The Formaldehyde Reactant

The formaldehyde reactant is suitably introduced in the pure form or is produced in situ, e.g., from paraformaldehyde or trioxane.

The Methylene and Oxymethylene Ester Products

The methylene and oxymethylene di- or bis-esters produced by the process of the invention are represented by formula II:

wherein $R^1$ and $R^2$ have the same significance as defined in formula (I) and n is a whole integer from 1 to 5 inclusive, preferably 1 or 2.

In terms of the carboxylic acid ester reactant represented by formula (I), the formaldehyde reactant and carbon monoxide, the over-all net reaction involved in the process of the invention is depicted by the following equation (2):

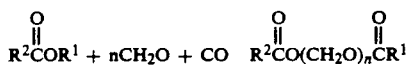

By way of illustration: (1) the reaction of methyl propionate or ethyl acetate, $CH_2O$ and CO, according to the process of the invention, produces an acetate propionate diester of the formula

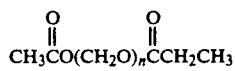

(2) the reaction of ethyl propionate, $CH_2O$ and CO produces propionate esters of the formula

and (3) the reaction of ethyl benzoate, $CH_2O$ and CO produces benzoate propionate diesters of the formula

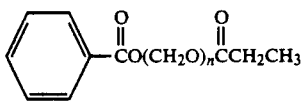

In the modification of the process wherein the carboxylic acid ester reactant is generated in situ from an ether, the overall net reaction is depicted by the following equation (3):

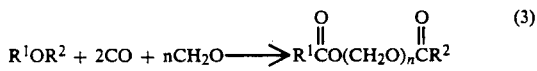

wherein $R^1$, $R^2$ and n have the same significance as defined above.

Reaction Conditions

The reactants employed in the process of the invention are generally contacted in the molar ratios defined by the stoichiometry of equation (2). That is, the molar ratio of carboxylic acid ester to carbon monoxide is substantially equimolar (e.g., 1.5:1 to 1:1.5). The amount of formaldehyde reactant depends in part upon the number of oxymethylene linkages ($CH_2O$) desired in the product. When a product comprising principally methylene bis-esters (wherein n=1) is desired, the molar ratio of formaldehyde to carboxylic acid ester is substantially equimolar (e.g., 1.5:1 to 1:1.5). When a product containing oxymethylene bis-esters (wherein n>1) is desired, molar ratios of formaldehyde to carboxylic acid ester of about 1:1.5 to 5:1 are employed. However, an excess of any reactant is suitably employed. For example, in some modifications of the process, it is desirable to employ excess of carbon monoxide or carboxylic acid ester as reaction diluents. Accordingly, molar ratios of carboxylic acid ester to carbon monoxide of from 10:1 to 1:10 are satisfactorily employed. When the carboxylic acid ester reactant is generated in situ from an ether, the molar ratio of ether to carbon monoxide is from 10:1 to 1:10, preferably 3:1 to 1:3.

The process of the invention is conducted in a fluid phase, i.e., either in the gaseous or liquid phase, in the presence or in the absence of an inert reaction diluent. Suitable inert normally liquid diluents are hydrocarbons free from aliphatic unsaturation such as hexane, heptane, octane, decane, cyclohexane, benzene, toluene and xylene. Preferred diluents are alkanoic acids of 1 to 6 carbon atoms, e.g., acetic, propionic, hexanoic, etc. As indicated above, alkanoic acids are suitable proton donors for the process of the invention. Accordingly, an alkanoic acid may serve as both the diluent and proton donor. Suitable normally gaseous diluents are nitrogen, hydrogen, argon, helium, methane and ethane. As indicated above, in some modifications of the process, a portion of the carbon monoxide or carboxylic acid ester reactant suitably serves as the reaction diluent. When diluent is employed, up to about 50 mols per mol of carboxylic acid ester reactant is satisfactory. The process is suitably conducted in an inert reaction environment so that the presence of reactive materials such as oxygen is desirably avoided.

The process of the invention is carried out by intimately contacting the carboxylic acid ester reactant and carbon monoxide in the presence of the transition metal catalyst, iodide or bromide promoter and proton donor. A variety of procedures can be employed for contacting the reaction components with the catalyst system. In one modification, the entire amounts of carboxylic acid ester reactant, carbon monoxide and catalyst components are charged to an autoclave or similar pressure reactor and maintained at reaction conditions for the desired reaction period. In another modification an active catalyst system is initially preformed by contacting at elevated temperature the transition metal compound, carbon monoxide, proton donor and iodide or bromide promoter in a suitable solvent and subsequently adding the remaining reaction components. In certain modifications wherein a supported transition metal catalyst is employed, the reaction is effected in a continuous manner as by passing a mixture of the reaction components and the remaining catalyst components through a reactor in which the supported transition metal catalyst is maintained.

The process of the invention is conducted at moderate temperatures and pressures. Suitable reaction temperatures varying from about 50° C. to 300° C. are satisfactory and reaction temperatures varying from about 150° C. to 250° C. are preferred. The process is conducted at or above atmospheric pressure, and pressures from about 1 atmosphere to about 100 atmospheres are satisfactory.

At the conclusion of the reaction, the product mixture is separated and the methylene and oxymethylene bis-ester product is recovered by conventional means such as fractional distillation. Unreacted reaction components and reaction products, such as alkanoid acids, are suitably recycled for further use in the process.

EXAMPLES

Example 1

Preparation of methylene bis-acetate

A 1-liter, magnetically stirred autoclave was charged with 0.001 mol of $Rh(CO)_2Cl$, sealed and flushed with nitrogen followed by carbon monoxide. The autoclave was then charged with 1 mol of methyl acetate, 1 mol of trioxane, 0.5 mol of acetic acid and 0.056 mol of hydrogen iodide. The autoclave was sealed, pressured to 1000 psig with carbon monoxide, and rapidly heated to 200° C. After 16 hours at 200° C., the reaction was terminated, the autoclave was opened and the reaction mixture analyzed by nuclear magnetic resonance spectroscopy, infrared spectroscopy and gas-liquid chromatography. The conversion of methyl acetate was 49% and the yield of methylene bis-acetate,

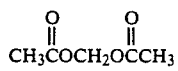

based on converted methyl acetate, was 28%.

Example 2

A 500-ml autoclave was charged with 0.001 mol of palladium dichloride, 0.5 mol methyl acetate, 0.25 mol acetic acid, and 0.052 mol of hydrogen iodide. The autoclave was pressured to 1000 psig with carbon monoxide and rapidly heated to 200° C. After 20 hours at 200° C. and a constant pressure of about 1000 psig, the reaction was terminated, the autoclave opened, and the reaction mixture analyzed by nuclear magnetic resonance spectroscopy, infrared spectroscopy and gas-liquid chromatography. The conversion of methyl acetate was 44% and the yield of acetic anhydride, based on converted methyl acetate, was 52%.

The production of acetic anhydride in this example demonstrates that if this example were repeated in the additional presence of about 0.5 mol of formaldehyde, methylene bis-acetate would be produced.

Example 3

A 1-liter, magnetically stirred autoclave was charged with 0.001 mol of $Rh(CO)_2Cl$, sealed and flushed with nitrogen followed by carbon monoxide. Dimethyl ether (1.18 mols), hydrogen iodide (0.05 mol), and acetic acid (0.5 mol) were then charged to the autoclave. The autoclave was sealed, pressured to 1000 psig with carbon monoxide and rapidly heated to 200° C. After 20 hours at 200° C., the reaction was terminated, the autoclave opened and the reaction mixture analyzed by nuclear magnetic resonance spectroscopy, infrared spectroscopy and gas-liquid chromatography. The conversion of dimethyl ether was 100%, the yield of methyl acetate, based on converted dimethyl ether, was 34% and the yield of acetic anhydride, based on converted dimethyl ether, was 43%.

If this example were repeated in the additional presence of about 1 mol of formaldehyde, methylene and oxymethylene bis-acetate would be produced.

Examples 4–11

The preparation of acetic anhydride and acetic benzoic anhydride from methyl acetate and methyl benzoate, respectively, was carried out by the following procedure.

A 1-liter, magnetically stirred autoclave was charged with the rhodium catalyst, sealed and flushed with nitrogen followed by carbon monoxide. The methyl ester, iodide or bromide promoter, solvent and proton source were then added to the autoclave. The autoclave was sealed, pressured to 1000 psig with carbon monoxide and rapidly heated (about 15 minutes) to reaction temperature.

The reaction was terminated after the indicated reaction time by an internal cooling coil and then vented through a dry-ice-cooled trap. The autoclave was opened and the reaction mixture analyzed by nuclear magnetic resonance spectroscopy, infrared spectroscopy and gas-liquid chromatography.

The methyl ester, rhodium catalyst, iodide or bromide promoter, proton donor, solvent, reaction conditions employed, and the results obtained are tabulated in Table I.

The reported yield of acetic acid is the acetic acid produced from the methyl ester and carbon monoxide reactants (i.e., excess over that present or derivable from the proton donor or solvent). When HI, HBr or acetic acid is reported as the proton donor, no additional amount over the amount of HI, HBr or acetic acid provided as the promoter or solvent was used. In Run 10, 0.004 mol of $AlCl_3.6H_2O$ was employed as a co-catalyst, and the water of crystallization of the rhodium catalyst and $AlCl_3$ co-catalyst was included in the 0.05 mol of $H_2O$ indicated in Table I.

If Examples 4–11 were repeated in the additional presence of about 1 mol formaldehyde, the corresponding bis-esters would be produced.

TABLE I

| | Carbonylation of Methyl Esters | | | | | | | |
|---|---|---|---|---|---|---|---|---|
| | Run | | | | | | | |
| | 4 | 5 | 6 | 7 | 8 | 9 | 10 | 11 |
| Methyl ester (1 mol) | acetate (0.5 mol) | acetate | acetate | acetate | acetate | acetate | acetate | benzoate |
| Rhodium catalyst (0.001 mol) | A | A | A | A | B | B | B | A |
| Promoter (0.05 mol) | HBr | Ch$_3$I | HI | HI* | HI | CH$_3$I | CH$_3$I | HI |
| Proton donor | HBr, acetic acid | acetic acid | HI, acetic acid | HI | HI, acetic acid | CH$_3$OH** | H$_2$O** | HI |
| Solvent (0.5 mol) | acetic acid | acetic acid (0.25 mol) | acetic acid | none | acetic acid | none | none | benzoic acid (0.25 mol) |
| Temperature, °C. | 200 | 150 | 200 | 200 | 200 | 200 | 200 | 200 |
| Time, hours | 18–20 | 17 | 17 | 16 | 19 | 16 | 8 | 17 |
| Maximum Pressure, psig | 1000 (initial) | 1275 | 1525 | 1500 | 1590 | 1800 | 1790 | 1620 |
| % Conversion methyl ester | 75 | 35 | 81 | 31 | 69 | 28 | 66 | 54 |

TABLE I-continued

| | Carbonylation of Methyl Esters | | | | | | | |
|---|---|---|---|---|---|---|---|---|
| | Run | | | | | | | |
| | 4 | 5 | 6 | 7 | 8 | 9 | 10 | 11 |
| % Yield acetic acid | 43.8 | — | 13 | 27 | 22 | 21 | 11 | — |
| % Yield acetic anhydride | 37.5 | 43 | 80 | 32 | 59 | 31 | 57 | 24*** |

Catalyst A = $Rh(CO)_2Cl$
Catalyst B = $RhCl_3 \cdot 3H_2O$
*0.065 mol
**0.05 mol
***as benzoic-acetic anhydride

What is claimed is:

1. A process for producing carboxylic acid anhydrides by reacting, in the fluid phase, a carboxylic acid ester of the formula $R^2CO_2R^1$, wherein $R^1$ is alkyl of 1 to 10 carbon atoms and $R^2$ is hydrogen, alkyl of 1 to 10 carbon atoms, phenyl, alkylphenyl of 7 to 10 carbon atoms or phenylalkyl of 7 to 10 carbon atoms, and carbon monoxide in the presence of catalytic amounts of a catalyst system consisting essentially of a rhodium compound, an iodide promoter and a proton donor, at a temperature of from about 50° C. to 300° C. and an initial pressure of from about 1 atmosphere to about 100 atmospheres, under substantially anhydrous reaction conditions.

2. The process of claim 1, wherein the proton donor is water or a Bronsted acid.

3. The process of claim 2, wherein $R^1$ is alkyl of 1 to 6 carbon atoms.

4. The process of claim 3, wherein $R^2$ is alkyl of 1 to 6 carbon atoms or phenyl.

5. The process of claim 4, wherein $R^1$ and $R^2$ are methyl.

6. The process of claim 4, wherein the Bronsted acid is acetic acid and the iodide promoter is hydroiodic acid.

7. The process of claim 4, wherein the proton donor and iodide promoter are hydroiodic acid.

8. The process of claim 4, wherein the rhodium compound is a rhodium halide or a rhodium carbonyl halide.

9. The process of claim 2, wherein the proton donor is an alkanoic acid of 1 to 6 carbon atoms.

10. The process of claim 1, wherein $R^1$ and $R^2$ are alkyl.

11. The process of claim 10, wherein the ester reactant is generated in situ from a dialkyl ether reactant.

12. The process of claim 11, wherein both alkyl groups of the dialkyl ether are the same linear alkyl group of 1 to 4 carbon atoms.

13. The process of claim 11, wherein the dialkyl ether is dimethyl ether.

14. The process of claim 11, wherein the Bronsted acid is acetic acid and the iodide promoter is hydroiodic acid.

15. The process of claim 11, wherein the rhodium compound is a rhodium halide or a rhodium carbonyl halide.

16. The process of claim 1, wherein the reaction is carried out at a temperature of about 150° to 250° C.

17. The process for producing acetic anhydride by reacting, in the fluid phase, methyl acetate and carbon monoxide in the presence of catalytic amounts of a catalyst system consisting essentially of a rhodium compound, an iodide promoter and a proton donor, at a temperature of from about 50° C. to 300° C. and an initial pressure of from about 1 atmosphere to about 100 atmospheres under substantially anhydrous reaction conditions.

18. A process for producing carboxylic acid anhydrides by reacting, in the fluid phase, a carboxylic acid ester of the formula $R^2CO_2R^1$, wherein $R^1$ is alkyl of 1 to 10 carbon atoms and $R^2$ is hydrogen, alkyl of 1 to 10 carbon atoms, phenyl, alkylphenyl of 7 to 10 carbon atoms or phenylalkyl of 7 to 10 carbon atoms, and carbon monoxide in the presence of catalytic amounts of a catalyst system comprising a rhodium compound, an iodide promoter and a proton donor, at a temperature of from about 50° C. to 300° C. and an initial pressure of from about 1 atmosphere to about 100 atmospheres, under substantially anhydrous reaction conditions.

19. A process for producing acetic anhydride by reacting, in the fluid phase, methyl acetate and carbon monoxide in the presence of catalytic amounts of a catalyst system comprising a rhodium compound, an iodide promoter and a proton donor, at a temperature of from about 50° C. to 300° C. and an initial pressure of from about 1 atmosphere to about 100 atmospheres under substantially anhydrous reaction conditions.

* * * * *